United States Patent
Schaefermeyer et al.

(10) Patent No.: US 6,640,138 B1
(45) Date of Patent: Oct. 28, 2003

(54) APPARATUS AND METHOD FOR HEAT TREATMENT OF TISSUE

(75) Inventors: Theron N. Schaefermeyer, North Salt Lake, UT (US); Aaron Perlmutter, New York, NY (US); Charles Manker, Lake Forest, IL (US)

(73) Assignee: TherMatrx, Inc., Northbrook, IL (US)

( * ) Notice: Subject to any disclaimer, the term of this patent is extended or adjusted under 35 U.S.C. 154(b) by 197 days.

(21) Appl. No.: 09/632,523

(22) Filed: Aug. 4, 2000

(51) Int. Cl.[7] .................................................. A61F 2/00

(52) U.S. Cl. ........................ 607/101; 607/105; 607/102; 604/97.03

(58) Field of Search ............................... 607/96, 98, 99, 607/101, 102, 105, 156, 154, 192, 193, 196, 198; 604/95.03, 96.01, 97.01, 97.03

(56) References Cited

U.S. PATENT DOCUMENTS

| | | |
|---|---|---|
| 2,936,761 A | 5/1960 | Snyder |
| 3,720,199 A | 3/1973 | Rishton et al. |
| 3,978,863 A | 9/1976 | Fettel et al. |
| 4,046,139 A | 9/1977 | Horn |
| 4,154,246 A | 5/1979 | LeVeen |
| 4,275,730 A | 6/1981 | Hussein |
| 4,311,154 A | 1/1982 | Sterzer et al. |
| 4,312,364 A | 1/1982 | Convert et al. |
| 4,403,618 A | 9/1983 | Turner et al. |
| 4,448,198 A | 5/1984 | Turner |
| 4,462,412 A | 7/1984 | Turner |
| 4,469,103 A | 9/1984 | Barrett |
| 4,522,194 A | 6/1985 | Normann |
| 4,524,550 A | 6/1985 | Ruggera et al. |
| 4,583,556 A | 4/1986 | Hines et al. |
| 4,586,516 A | 5/1986 | Turner |
| 4,589,423 A | 5/1986 | Turner |
| 4,601,296 A | 7/1986 | Yerushalmi |
| 4,632,669 A | 12/1986 | Phipps, Sr. et al. |

(List continued on next page.)

FOREIGN PATENT DOCUMENTS

| | | |
|---|---|---|
| DE | 2815156 | 10/1978 |
| DE | 3534124 | 4/1987 |
| EP | 0105677 | 4/1984 |
| EP | 0370890 | 5/1990 |
| SU | 1512622 | 10/1989 |
| WO | WO 81/03616 | 12/1981 |
| WO | WO 89/11311 | 11/1989 |
| WO | WO 97/01374 | 1/1997 |
| WO | WO 99/58194 | 11/1999 |

OTHER PUBLICATIONS

Astrahan et al., "Microwave Applicator for Transurethral Hyperthermia of Benign Prostate Hyperplasia", International Journal of Hyperthermia, 5 (3), pp. 283–296 (May/Jun. 1989).

(List continued on next page.)

*Primary Examiner*—Roy D. Gibson
(74) *Attorney, Agent, or Firm*—McCormick, Paulding & Huber LLP

(57) ABSTRACT

An energy radiation applicator apparatus for hyperthermic treatment of targeted tissue in a patient is provided. The apparatus comprises a catheter for insertion into the patient, and an applicator operatively attached to the catheter and an energy source sufficient for elevating the temperature of targeted tissue in proximity to the applicator to a preselected temperature and for maintaining the preselected temperature during treatment. It may also comprise a positioning mechanism operatively attached to the catheter so that the applicator may be positioned at a desired position in proximity to the targeted tissue to be treated, a temperature sensor operatively attached to the catheter and in operative association with the applicator for measuring the temperature of the targeted tissue, and a locator for determining whether the applicator remains at the desired position. The locator is operatively attached to the energy source and deactivates the energy source when the conditions exist that permit the applicator to move from the desired position.

31 Claims, 6 Drawing Sheets

U.S. PATENT DOCUMENTS

| | | | |
|---|---|---|---|
| 4,638,813 | A | 1/1987 | Turner |
| 4,658,836 | A | 4/1987 | Turner |
| 4,662,383 | A | 5/1987 | Sogawa et al. |
| 4,669,475 | A | 6/1987 | Turner |
| 4,672,980 | A | 6/1987 | Turner |
| 4,676,258 | A | 6/1987 | Inokuchi et al. |
| 4,681,122 | A | 7/1987 | Winters et al. |
| 4,700,716 | A | 10/1987 | Kasevich et al. |
| 4,712,559 | A | 12/1987 | Turner |
| 4,790,821 | A | 12/1988 | Stines |
| 4,798,215 | A | 1/1989 | Turner |
| 4,813,429 | A | 3/1989 | Eshel et al. |
| 4,860,744 | A | 8/1989 | Johnson et al. |
| 4,860,752 | A | 8/1989 | Turner |
| 4,891,483 | A | 1/1990 | Kikuchi |
| 4,967,765 | A | 11/1990 | Turner et al. |
| 4,974,587 | A | 12/1990 | Turner et al. |
| 5,003,991 | A | 4/1991 | Takayama |
| 5,007,437 | A | 4/1991 | Sterzer |
| 5,045,051 | A | 9/1991 | Midler et al. |
| 5,056,528 | A | 10/1991 | Zytkovicz et al. |
| 5,057,106 | A | 10/1991 | Kasevich et al. |
| 5,097,844 | A | 3/1992 | Turner |
| 5,197,940 | A | 3/1993 | Sievert et al. |
| 5,209,725 | A | 5/1993 | Roth |
| 5,220,927 | A | 6/1993 | Astrahan et al. |
| 5,234,004 | A | 8/1993 | Hascoet et al. |
| 5,249,585 | A | 10/1993 | Turner et al. |
| 5,300,099 | A | 4/1994 | Rudie |
| 5,344,435 | A | 9/1994 | Turner et al. |
| 5,354,325 | A | 10/1994 | Chive et al. |
| 5,366,490 | A | 11/1994 | Edwards et al. |
| 5,460,628 | A * | 10/1995 | Neuwirth et al. ............ 606/27 |
| 5,509,929 | A * | 4/1996 | Hascoet et al. ........ 604/170.03 |
| 5,531,676 | A | 7/1996 | Edwards et al. |
| 5,542,916 | A | 8/1996 | Hirsch et al. |
| 5,571,153 | A | 11/1996 | Wallstén |
| 5,599,301 | A | 2/1997 | Jacobs et al. |
| 5,616,114 | A | 4/1997 | Thornton et al. |
| 5,620,480 | A | 4/1997 | Rudie |
| 5,941,898 | A | 8/1999 | Moenning et al. |
| 5,954,714 | A * | 9/1999 | Saadat et al. ................. 606/28 |
| 5,971,973 | A | 10/1999 | Peters |
| 5,980,485 | A | 11/1999 | Grantz et al. |
| 6,021,781 | A * | 2/2000 | Thompson et al. ......... 128/898 |
| 6,216,703 | B1 | 4/2001 | Manker et al. |

OTHER PUBLICATIONS

Bernier et al. "Thermal Therapy in the Treatment of Benign Prostatic Hyperplasia" *Current Opinion in Urology*, vol. 7, pp. 15–20 (1997).

Baba et al., "Transurethral Microwave Thermotherapy for Benign Prostatic Hyperplasia," *Journal of Endourology*, 6(5): 371–376 (1992).

Baert et al. "Transurethral Microwave Hyperthermia for Benign Prostatic Hyperplasia: Preliminary Clinical and Pathological Results" *Journal of Urology,* 144 pp. 1383–1387 (Dec. 1990).

Baert et al. "Transurethral Microwave Hyperthermia for Benign Prostatic Hyperplasia: The Leuven Clinical Experience" *Journal of Endourology,* 7(1) pp. 61–69 (1993).

Beaven et al., "The Treatment of Urinary Retention With Transurethral Microwave Thermotherapy," 251–254 (1992) in *Prostatron 1997 Theramotherapy Compendium (Re–Published by EDAP Technomed, Inc. Cambridge, Mass.).*

Bhanot et al. "A Radiofrequency Method of Thermal Tissue Ablation for Benign Prostatic Hyperplasia" *Urology*, vol. 45 (No. 3) pp. 427–434. (Mar. 1995).

Blute, 3 pages *Reprinted From A.U.A. Today,* 6(11) (1993) in *Prostatron 1997 Theramotherapy Compendium (Re–Published by EDAP Technomed, Inc. Cambridge, Mass.).*

Blute et al., "Transurethral Microwave Thermotherapy for Management of benign prostatic Hyperplasia: Results of the United States Prostatron Cooperative Study," *The Journal of Urology,* 150:1591–1596 (1993).

Blute, "Microwave Thermotherapy for the Treatment of Benign Prostatic Hyperplasia," *Seminars in Urology,* XII(3): 181–191 (1994).

Carter et al. "Single–Session Transurethral Microwave Thermotherapy for the Treatment of Benign Prostatic Obstruction" *Journal of Endourology,* vol. 5 (No. 2) pp. 137–144 (1991).

Constable et al, "Perturbation of the Temperature Distribution in Microwave Irradiated Tissue Due to the Presence of Metallic Thermometers", *Med. Phys.*, 14(3), pp. 385–388 (May/Jun. 1987).

Corica et al. "Transurethral Radio Frequency Thermotherapy for Syptomatic Benign Prostatic Hyperplasia"*EurUrol* , vol. 23, pp. 312–317 (1993).

"Critical Evaluation of Treatment Modalities in Local Hyperthermia of the Prostate" pp. 336–337 in *Benign Prostate Hyperplasia: Innovation in Management,* Petrovich & Baert (Eds.) Springer Verlag Publishing (1994).

De la Rosette et al. "Current Status of Thermotherapy of the Prostate" *The Journal of Urology* vol. 157, pp. 430–438 (Feb. 1997).

De Wildt et al., "Transurethral Microwave Thermotherapy: An Evolving Technology in the Treatment of Benign Prostatic Enlargement," *British Journal of Urology,* 76:531–538 (1995).

Devonec et al., "Clincial Response to Transurethral Microwave Thermotherapy is Thermal Dose Dependent," *Eur. Urol.* 23:267–274 (1993).

Devonce et al., *Curr. Opinion in Urology,* 5: 3–9 (1995).

Devonec et al., "Microwave Thermotherapy in Benign Prostatic Hypertrophy," *Curr. Opinion in Urology,* 3:202–208 (1993).

Devonec et al. "Review: Transurethral Microwave Thermotherapy in Benign Prostatic Hyperplasia" *Journal of Endourology,* vol. 7 (No. 3) pp. 255–259 (1993).

Devonec et al. "Transurethral Microwave Heating of the Prostate—Or from Hyperthermia to Thermotherapy", *Journal of Endourology,* vol. 5 (No. 2) pp. 129–135 (1991).

Devonec et al. "Transurethral Microwave Thermotherapy (TUMT)" 1992 *Monographs in Urology™,* vol. 13 (No. 4) pp. 77–95. Stamey, Thomas A., Editor.

Diederich et al. "Combination of Implantable and Transurethral Ultrasound Applications for Prostate Thermal Therapy" *Proceedings of the 1997 IEEE Ultrasonics Symposium,* Ontario, Canada, Oct. 5–8, 1997. Vol. 2, pp. 1337–1340 (Oct. 5, 1997).

Diederich et al., "Induction of Hyperthermia Using an Intracavitary Multielement Ultrasonic Applicator," *IEEE Transactions on Biomedical Engineering,* 36(4), (Apr., 1989).

Ding Jen Lee, et al., "A New Design of Microwave Interstitial Applicator for Hyperthermia with Improved Treatment Volume", *Int. J. Radiation Oncology Biol. Phys,* 12, pp. 2003–2008 (Nov. 1986).

Ding–Jiu Li, et al., "Design & Thermometry of an Intracavitary Microwave Applicator Suitable for Treatment of Some Vaginal & Rectal Cancers", *Int. J. Radiation Oncology Boil. Phys.,* 10, pp. 2155–2161 (Nov. 1984).

Dunscomde et al., "Heat Production in Microwave–Irradiated Thermocouples", *Med. Phys.* 13(4), pp. 457–461 (Jul./Aug. 1986).

El–Deek M. El–Sayed et al., "Use of Sheath Helix Slow––Wave Structure as an Applicator in Microwave Heating Systems", *Journal of Microwave Power,* 16(3 and 4), pp. 283–288 (1981).

Harada, et al., "Microwave Surgical Treatment of Diseases of Prostate", *Urology,* 26(6), pp. 572–576 (Dec. 1985).

Höfner et al., "Changes In Outflow Obstruction Following Transurethral Microwave Thermotherapy," (*Original Source Unknown*),(1995) *in Prostatron 1997 Theramotherapy Compendium (Re–Published by EDAP Technomed, Inc. Cambridge, Mass.*).

Homma et al., "Transurethral Microwave Thermotherapy for benign prostatic Hyperplasia: A 2–Year Follow–Up Study," *Journal of Endourology,* 7:261–265 (1993).

IEEE Transactions on Biomedical Engineering, 36 (4), 432–438 (1989).

Leybovich, et al., "Intracavitary Hyperthermia: A Newly Designed Applicator for Tracheal Tumors", *Endocurietherapy/Hyperthermia Oncology,* 3, pp. 23–29 (Jan. 1987).

Linder et al., "Local Hyperthermia of the Prostate Gland for the Treatment of Bening Prostatic Hypertrophy and Urinary Retention" *British Journal of Urology,* 1987, 60, pp. 567–571.

McGuire, R. "Transurethral Hyperthermia for BPH: Trial's Goal is to Top 80% Success," Medical Tribune, 29 (9), pp. 3,13,14 (Mar. 31, 1988).

ProstaLund, "ProstaLund Feedback Treatment of BPH", www.prostalund.com.

ProstaLund, "About BPH" www.prostalund.com.

Mendeckie et al., "Microwave Applicators for Localized Hyperthermia Treatment of Cancer of the Prostate", *Int. J. Radiation Boil. Phys.,* 6(11), pp. 1583–1588 (Nov. 1980).

Perlmutter, "Prostatic Heat Treatments" *in Alternate Methods in the Treatment of Benign Prostatic Hyperplasia (Romas and Vaughan, Eds.)* pp. 133–155 (1993).

Sapozink et al. "Transurethral Hyperthermia for Benign Prostatic Hyperplasia: Preliminary Clinical Results" *The Journal of Urology,* vol. 143, pp. 944–950 (May 1990).

Satoh et al., "Thermal Distribution Studies of Helical Coil Microwave Antennas for Interstitial Hyperthermia," *Int'l J. Radiation Oncology Biol. Phys.,* 15, pp. 1209–1218.

Taylor et al., "Electromagnetic Syringe" *IEEE Transactions on Biomedical Engineering,* BME 25 (3) (May, 1978).

"Treatment Results with Transurethral Hyperthermia in Patients with Benign Prostatic Hyperplasia" pp. 317–326 in *Benign Prostate Hyperplasia: Innovations in Management,* Petrovich, Ameye & Baert (Eds.) Springer Verlag Publishing (1994).

Tubaro et al., "Transurethral Microwave Thermotherapy in the Treatment of Symptomatic Benign Prostatic Hyperplasia," *Eur. Urol.* 23: 285–291 (1993).

Vandenbossche et al. "(TURF) Transurethral Radiofrequency Heating for Benign Prostatic Hyperplasia at Various Temperatures with Thermex II®: Clinical Experience" *Eur. Urol,* vol.23, pp. 302–306 (1993).

Viguier et al. "Benign Prostatic Hypertrophy Treatment by Transurethral Radiofrequency Hyperthermia with Thermex II", *Eur. Urol,* vol. 23, pp. 318–321 (1993).

Walden et al., "How to Select Patients Suitable for Transurethral Microwave Thermotherapy: A Systematic Evaluation of Potentially Predictive Variables," *British Journal of Urology,* 81: 817–822 (1988).

Watson et al., "Heat Treatment for Severe, Symptomatic Prostatic Outflow Obstruction," *World Journal of Urology,* 9:7–11 (1991).

Wu, et al., "Performance Characteristics of a Helical Microwave Interstitial Antenna for Local Hyperthermia", *Med. Phys,* 14(2), pp. 235–237 (Mar./Apr. 1987).

Yerushalmi et al., "Localized Microwave Hyperthermia in the Treatment of Poor Operative Risk Patients with Benign Prostatic Hyperplasia", Williams & Wilkins, Co. vol. 133, pp. 873–876 (May 1985).

\* cited by examiner

APPARATUS AND METHOD FOR HEAT TREATMENT OF TISSUE

BACKGROUND OF THE INVENTION

1. Field of the Invention

This invention relates to energy radiation devices for medical hyperthermic treatments and, more particularly, to a combined catheter and energy applicator for treating prostatomegaly such as benign prostatic hypertrophy, prostatitis, and prostate malignancy.

2. State of the Art

Hyperthermia or induced high body temperature has been considered beneficial in treating various human diseases including many types of cancer. More specifically, various types of malignant growths are considered by many researchers to have a relatively narrow hyperthermia treatment temperature range. Below a threshold temperature of about 41.5 degrees Celsius, thermal destruction of these malignancies is generally not possible, and may even stimulate their growth. However, at temperatures above a range of about 43 to 45 degrees Celsius, thermal damage to most normal body tissue cells occurs if exposure lasts for even a relatively short duration.

While some types of superficial cancers are known to respond to direct application of surface heat, deeply located or subsurface malignant growths, owing to limited penetration depth of externally applied energy, tissue blood flow, and heat transfer properties of the body, are more difficult to heat to the desired temperature without damaging overlying and adjacent healthy tissue. A solution to this problem has been the development of radiation heating devices for inducing hyperthermia. This form of treatment is historically known as "diathermia."

Radiation heating of subsurface growths from an exterior surface using, for example, electromagnetic (EM) or ultrasound (US) radiation, is ordinarily enabled by the configuration and placement of one or more applicators and by appropriate selection of EM or US radiation frequency, phase and intensity. Nevertheless, tissue growths inside of, or in close proximity to, heat sensitive tissue or organs, are much more effectively and safely heated by radiation irradiating applicators positioned within the body as close as possible to the growth requiring treatment.

The advantages of positioning radiation applicators relatively close to the growth to be heated by radiation include more direct treatment of the enlarged tissues causing the undesirable symptoms. It also permits improved heating control, more localized heating, and consequently less possibility of overheating adjacent healthy tissue.

Close applicator access to certain types of diseased tissue growth may be provided by surgical procedures for naturally occurring body passages such as the esophagus, larynx, urethra, prostate gland and colon. Surgical procedures may enlarge the passage by cutting away the diseased tissue. Some heating methods use small radiation applicators placed over the tissue or in an incision to provide direct irradiation of the growth.

Special and difficult problems often attend growths found along natural body passages. For example, diseased tissue tends to spread around and along the passage, often in a relatively thin layer. Typically, patient problems may originate from a tissue layer which is less than one centimeter thick, and may extend as far as 6–10 centimeters along the passage. Care must be taken to avoid the use of applicators which may result in nonuniform radiation heating of the elongated growth. To make one end of the applicator hot enough to kill the unwanted elongated growth, it may be necessary to make the temperature at the other end of the applicator so hot that it may kill surrounding healthy tissue. To treat a longer tissue along the urethra or other passage, multiple treatments of short, adjacent lengths of tissue may be necessary with the antenna manually repositioned along the urethra between each treatment.

Attempts to properly position the applicator in proximity to the targeted tissue include the use of balloon catheters, which utilize pressurized fluid to inflate the balloon in the neck of the bladder, thereby positioning and maintaining the applicator at a desired position in proximity to the targeted tissue. A lack of a reliable method to determine the position of the applicator and whether the applicator has moved during the treatment may result in inconsistent treatment results or unwanted heating of healthy tissue. Consequently, care must be taken to insure that the applicator remains at the desired position in response to deflation of the balloon or other movement of the catheter.

SUMMARY AND OBJECTS OF THE INVENTION

Accordingly, it is an object of the invention to provide an improved energy radiation device for medical hyperthermic treatment.

Another object of the invention is to provide an urethral insertable energy applicator for treating benign prostatic hyperplasia or other tissue diseases associated with the urinary tract.

A further object of the invention is to provide an urethral insertable energy applicator which can be positioned with respect to the prostate and maintained against movement therefrom during treatment.

A more specific object of the invention is to provide a system for determining whether the energy applicator has moved or may move during treatment and to signal the operator and/or deactivate a power source in response to such conditions. A related object is to provide an urethral insertable energy applicator for treating BPH which includes a system for determining whether conditions exist in which the applicator may move during treatment and signal the operator of such conditions.

These and other features and advantages of the invention will be more readily apparent upon reading the following description of a preferred exemplified embodiment of the invention and upon reference to the accompanying drawings.

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DETAILED DESCRIPTION OF THE PREFERRED EMBODIMENT

Referring now to the figures, a radiation applicator system 10 in accordance with the invention is shown. The radiation applicator system 10 may include a catheter 12 insertable into a patient's body through, for example, the urethra or other passage, a radiation applicator generally referenced as 14 for radiating energy into targeted tissue using a radiation heating antenna 15, a positioning mechanism, such as a balloon, for positioning and maintaining the catheter 12 at a desired position, and, in accordance with certain objects of the invention, a locator mechanism generally referenced as 18 for determining whether the heating antenna 15 remains at the desired position. The structure and operation of the radiation applicator system 10 will be described in connection with a urinary catheter for the treatment of BPH, but is, of course, applicable to other medical hyperthermic treatments. Other exemplary radiation applicators and catheters suitable for use with the system 10 in accordance with the invention are described in U.S. Pat. Nos. 4,967,765 to Turner et al., U.S. Pat. No. 5,220,927 to Astrahan et al., U.S. Pat. No. 5,249,585 to Turner et al., and U.S. Pat. No. 5,344,435 to Turner et al., which are hereby incorporated by reference.

Figure 1:
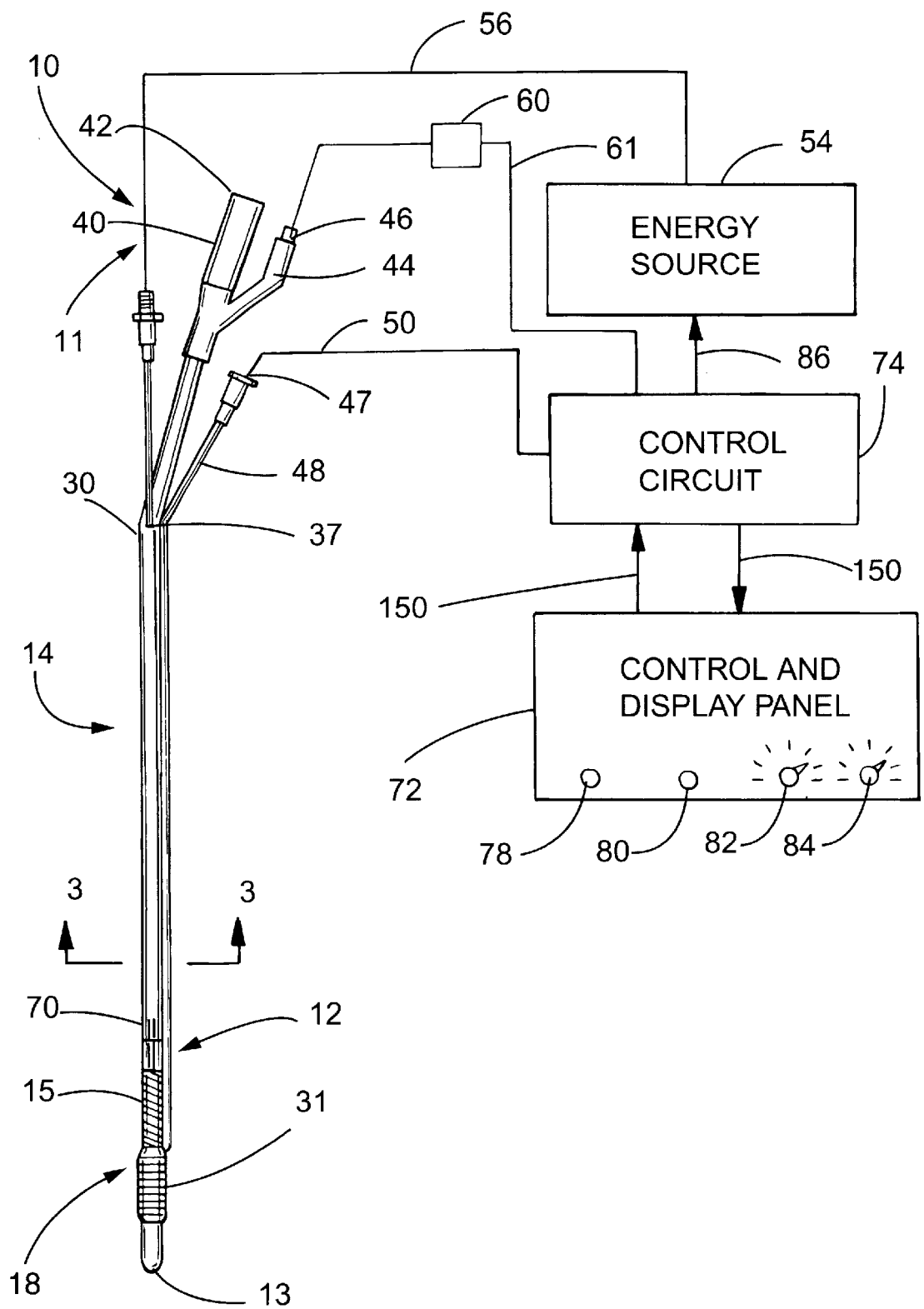
FIG. 1 is a view of one embodiment of an energy radiation device for medical hyperthermic treatment in accordance with the invention.
Figure 2:
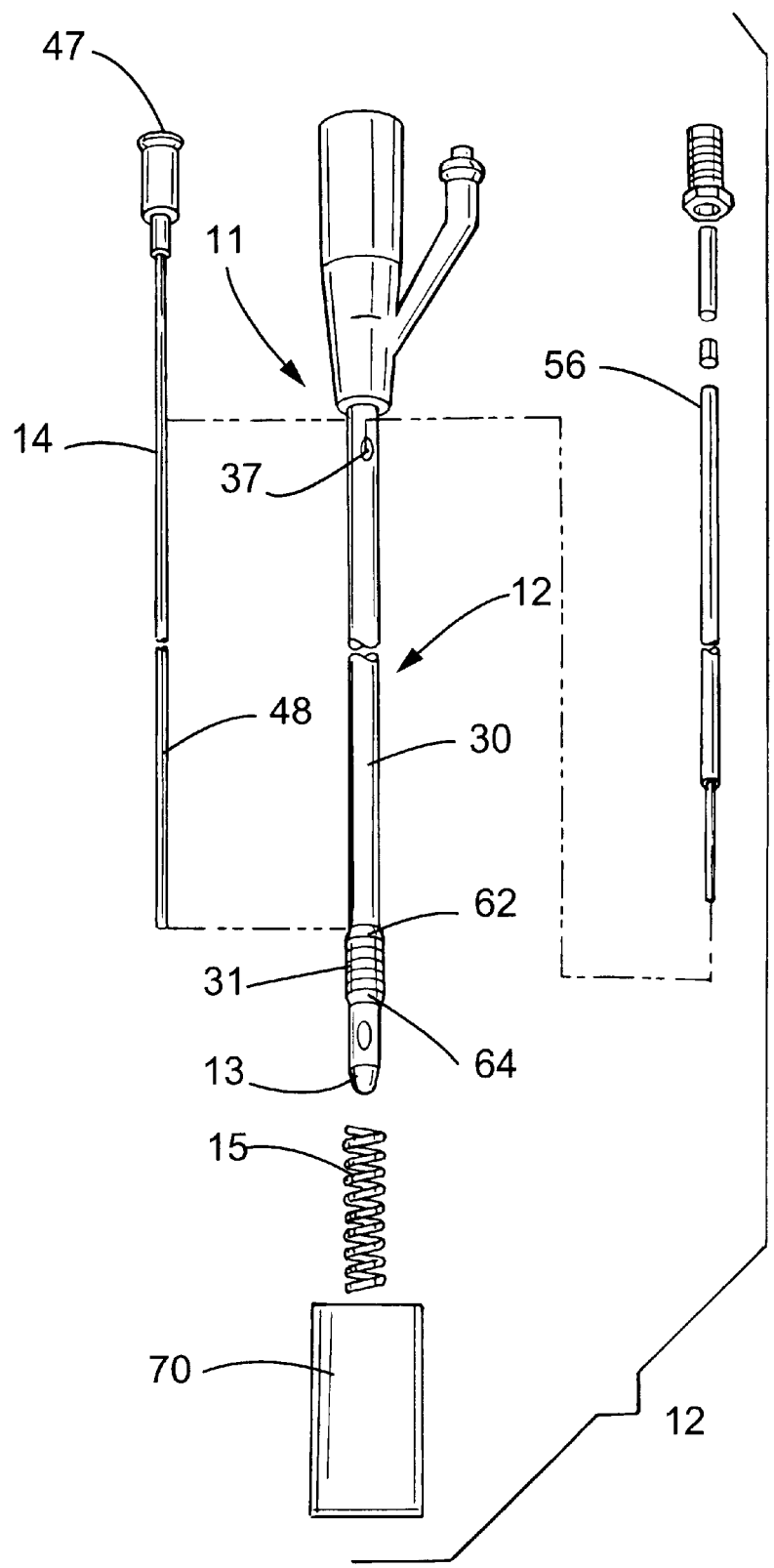
FIG. 2 is an exploded view of an urethral insertable catheter shown in FIG. 1.
Figure 3:
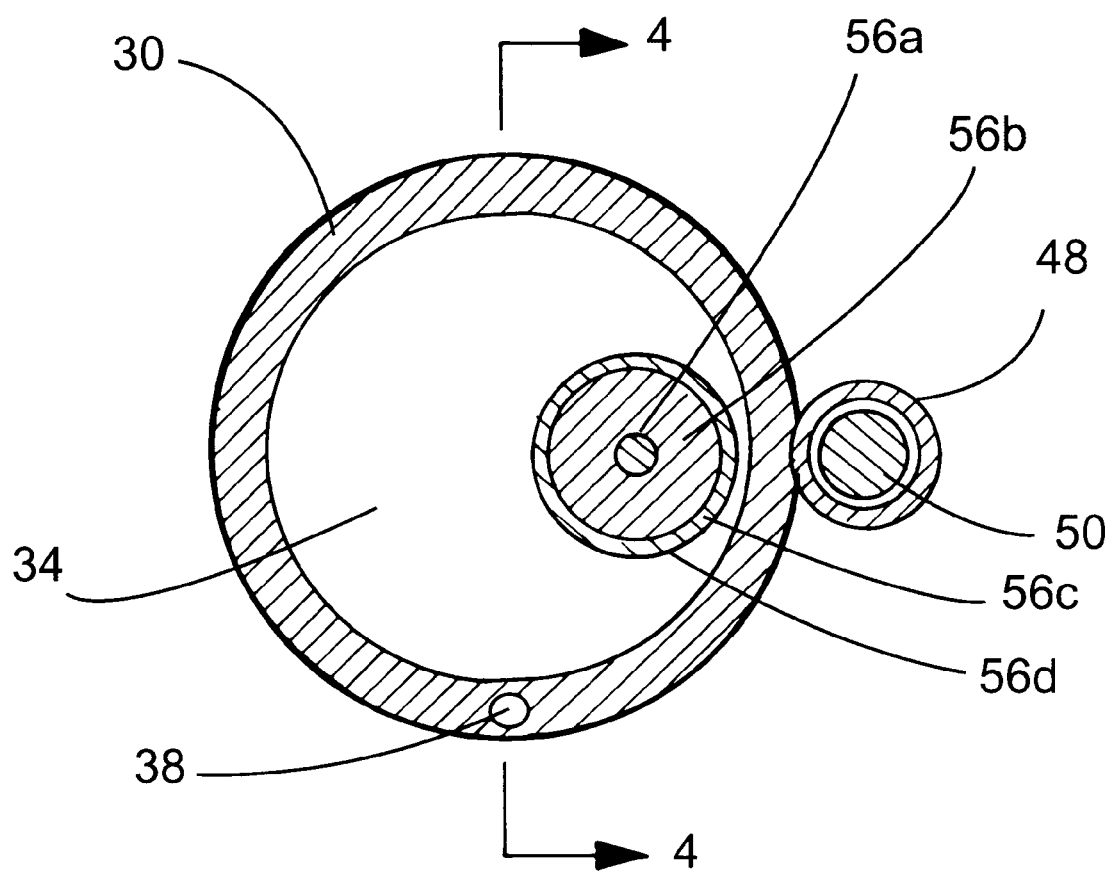
FIG. 3 is a cross-sectional view of the catheter taken along line 3—3 in FIG. 1.

Referring to FIGS. 1–3, the exemplary catheter 12 may be, for example, a balloon type urinary catheter having a flexible, plastic tubular body 30 and a balloon 31. The catheter has at least one passage. The body 30 of the exemplary catheter, best shown in FIG. 3, may have a drainage passage 34, and a pressurized fluid passage 38 defined by the catheter walls for inflating a balloon 31. The catheter 12 may also have at least one sensor passage 48 for receiving a corresponding temperature sensor 50 capable of measuring the temperature of the tissue surrounding the catheter 12. The catheter 12 has a proximal end 11 closest to a power source 54 and a distal or insertion end 13 farthest from the power source 54. In other embodiments, the catheter may have other passages such as separate drainage and applicator passages.

A bifurcated access fitting 40 located at the proximal end 11 of the tubular body 30 facilitates communication with the passages in the body 30. The access piece 40 has a first opening 42 for connecting the central drainage passage 34 to a waste receiving receptacle (not shown) and a second opening 44 for introducing a pressurized fluid into passage 38 to inflate the balloon 31.

It will be appreciated that the catheter may have a positioning mechanism for positioning the antenna 15 to a desired position relative to the targeted tissue. One approach has been to utilize a catheter having an integral balloon 31, disposed at the distal end 13 of the catheter 12, and in open communication with the outlet of the pressurized fluid passage 38 to facilitate inflation and deflation of the balloon 31. The balloon 31 may be disposed between the stops 62 and 64 formed on the tubular body 30. An injection valve 46 attached to the fitting opening 44 controls the inflation of the balloon 31 and the retention of the balloon filling fluid. An exemplary valve 46 opens when a syringe (not shown) is inserted to supply pressurized fluid, such as air or water, to inflate the balloon 31. The valve 46 closes to retain the pressurized fluid in the balloon 31 when the syringe is removed.

Figure 6:
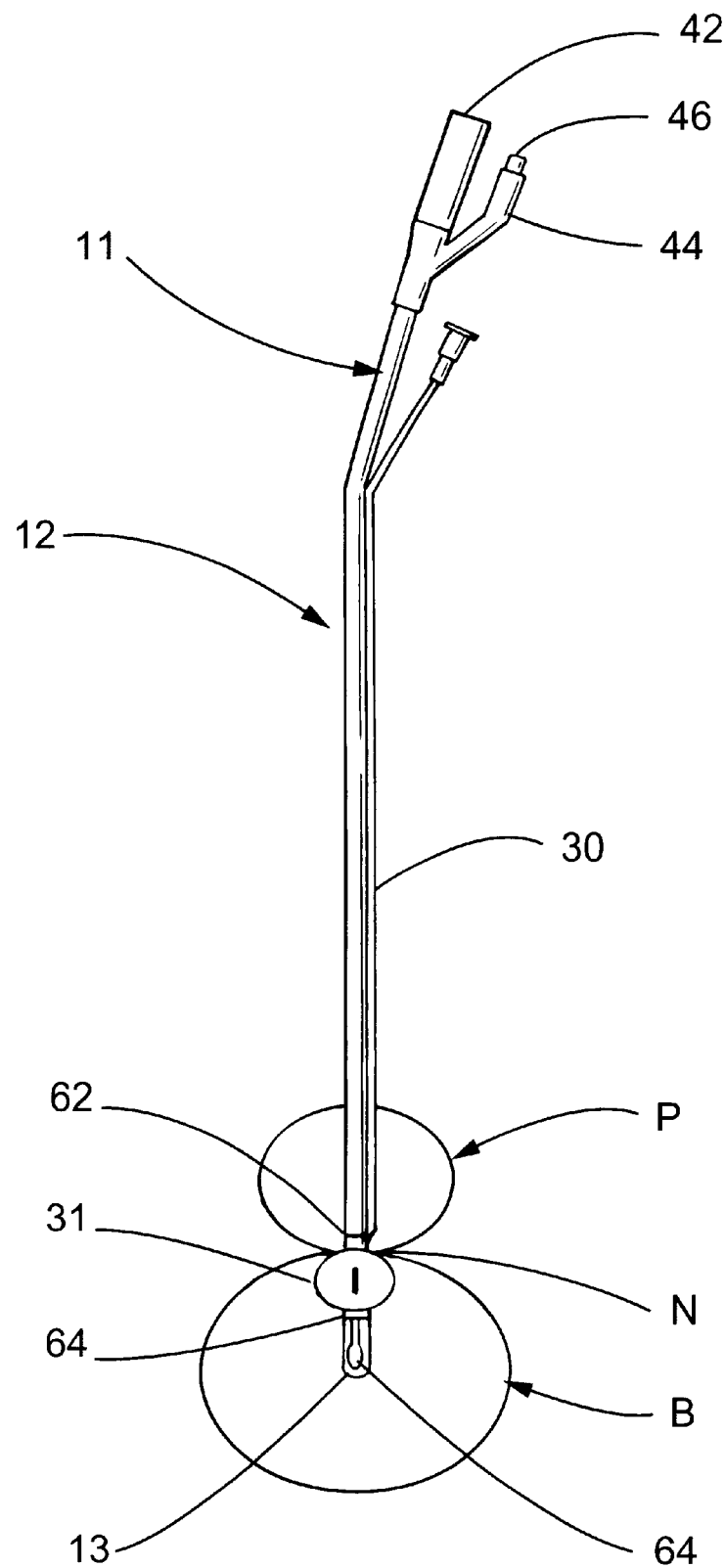
FIG. 6 is a schematic view of the catheter positioned inside a bladder and prostate of a patient.

In use, the distal end 13 of the catheter 12 is inserted through the patient's urethral passage and the prostate P, and into the bladder B, as schematically shown in FIG. 6. When the distal end 13 of the catheter 12 is in the bladder, pressurized fluid is introduced through valve 46 and fitting 40 into passage 38 to inflate balloon 31 within the bladder B. With the balloon 31 inflated in the bladder B, the catheter 12 is pulled slightly outwardly so that the balloon 31 seats in the neck N of the bladder B. This positively locates and positions the catheter 12 with respect to the bladder B and prostate P immediately adjacent to the bladder B as shown in FIG. 6. It effectively anchors the antenna 15 and minimizes and, preferably, eliminates any movement of the antenna 15 for the duration of the hyperthermic treatment. The interior of the balloon 31 may, for example, also have a ribbed configuration to minimize adhesion of the balloon to the shaft.

In accordance with certain objects of the invention, the energy applicator 15 may be placed at a known and predetermined position relative to the distal end 13 of the catheter 12 and the balloon 31. Consequently, when the position of the balloon 31 is fixed in relation to the prostate P, the position of antenna 15 relative to the prostate remains fixed and constant throughout treatment and the accurate placement of the applicator 14 in the prostate is repeatable from treatment to treatment and from patient to patient. The ability to accurately place the antenna 15 relative to the prostate P without complicated probing, visual imaging, or other positioning procedures, and the stability of the positioning so that the position relative to the prostate P remains constant during treatment, is an important aspect of the invention and important to the practical hyperthermic treatment of the prostate P.

It is also desirable that the position of the catheter 12 remain constant with respect to the bladder B and prostate P during the treatment regardless of any variation in length of the urethral passage during treatment. Movement of the applicator 14 and the antenna 15 during treatment away from the targeted tissue may cause healthy tissue to be heated. In accordance with certain objects of the invention, the system 10 has a locator mechanism generally designated 60 for determining whether the applicator 14 is properly positioned relative to the targeted tissue. The locator mechanism 60 is connected via signal cable 61 to the control circuit 74. In one embodiment, the locator mechanism 60 monitors the positioning mechanism to determine whether conditions exist that permit movement of the applicator antenna 15. An exemplary locator mechanism 60 may include a pressure monitor, such as a pressure transducer, for monitoring the pressure within the pressurized fluid passage 38 and balloon 31. In response to a pressure decrease, indicating that the balloon 31 has deflated and/or ruptured so that the antenna 15 may move from the predetermined location relative to the targeted tissue, the locator mechanism 60 in the form of a pressure monitor signals the power source 54 for the applicator 14 to be deactivated before any damage to non-targeted tissue may occur. Alternatively, the pressure transducer may activate a visual or auditory signal to alert the operator of the possibility of movement of the antenna 15 so the operator may deactivate the power source 54. The pressure monitor may be positioned in proximity to or communication with the injection valve 46 of the catheter 12.

The locator mechanism 60 may also be a pressure switch which is actuated in the presence of predefined pressure levels. The exemplary pressure switch may have activated and deactivated positions which activate or deactivate, respectively, the power source 54 for applicator 14. Back pressure within the desired pressure range in the pressure passage 38 and balloon 31 positions the switch to the activated position, thereby activating the power source 54. However, in response to a decrease in the pressure, indicating deflation of the balloon 31 and the potential for movement of the antenna 15, the switch moves to the deactivated position and signals for deactivation of the power source.

Another embodiment of the locator mechanism may include an optical sensor (not shown) operatively attached to the opening 42 of the drainage passage 34 and the control circuit 74 which measures, for example, dye levels in the balloon 31 and the passage 34. Optically sensitive dye may be placed in the balloon. Dye leakage from the balloon would cause increased dye levels within the drainage passage 34 so that the sensor, upon measuring the increased dye levels, may deactivate the power source or send another appropriate signal to the operator. Yet another locator mechanism may include a monitor, for example, that measures relative movement of the catheter within the urethra. The monitor may be attached to the patient, for example, so that movement of the patient does not erroneously indicate movement of the catheter within the urethra. In response to movement of the catheter and ultimately the antenna 15 within the urethra that exceeds predetermined limits, the locator mechanism deactivates the power source. Various additional modifications of the locator mechanism specifically illustrated and described herein will be apparent to those skilled in the art, particularly in light of the teachings of this invention. The invention should not be construed as limited to the specific form shown and described herein.

Figure 4:
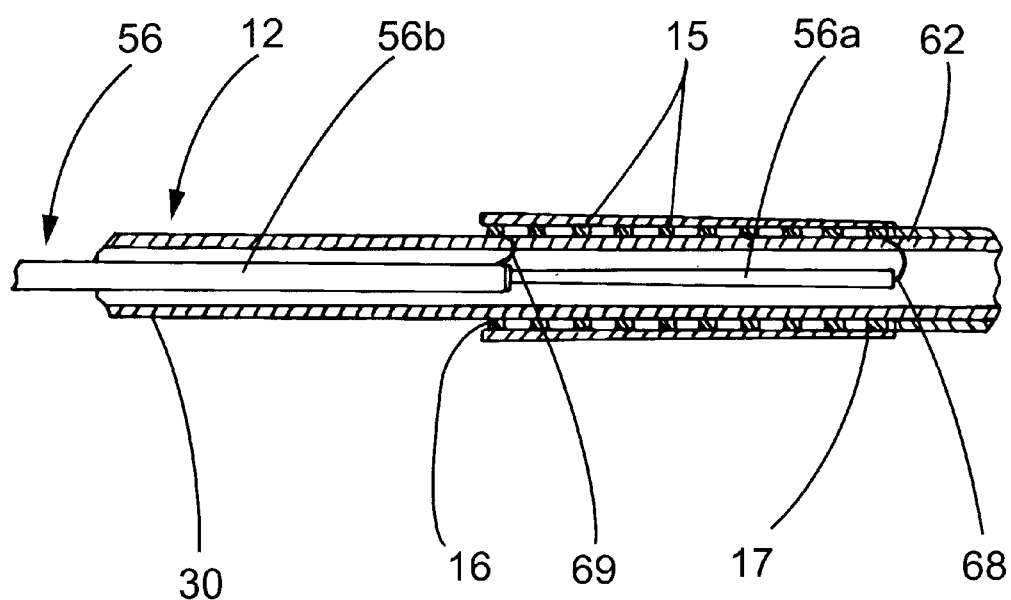
FIG. 4 is an enlarged fragmentary section of the catheter taken along line 4—4 in FIG. 3.

The system 10 requires at least one radiation applicator 14 having a radiating antenna 15 for conducting heat energy, such as electromagnetic (EM) radiation, ultrasound (US) radiation or other heat sources, to heat the targeted tissue to a desired temperature, typically about 41.5 to about 80 degrees Celsius. The antenna 15 may include a microwave helical coil, a metallic surface or other suitable configuration adapted to radiate the targeted tissue with energy. As best shown in FIG. 4, the antenna 15 has a distal end 17 farthest from the power source 54 and a proximal end 16 closest to the power source. The antenna 15 may be positioned adjacent a stop 62 inboard of the catheter balloon 31.

The antenna 15 may be connected to an energy or power source 54 by a transmission line, such as coaxial cable 56, dimensioned to fit within the drainage passage 34. While any suitable transmission line may be used, the exemplary cable 56 shown in FIG. 3 has an inner conductor 56a, an insulator 56b, an outer metal braided cover 56c and a cover 56d such as a silicon tube, to protect the cable from urine. In the exemplary embodiment shown in FIG. 4, the cable 56 may pass through at least the proximal end 16 and along the center axis of the antenna coil 15. The distal and proximal ends 17, 16 of the antenna 15 may be connected for example, by soldering wires 68 and 69 to the inner conductor 56a and the braided cover 56c, respectively.

The antenna coil 15 may also contain one or more of the following physical features:

(a) open or closed connection to the tip of the coil and center coaxial conductor;
(b) open or closed connection to the base of the coil and the outer coaxial conductor;
(c) conductor breaks or gaps within the coil winding;
(d) multiple coils stacked longitudinally and connected to individual coaxial cables to allow modification of the heat pattern length using either coherent or non-coherent phase energy into each coil;
(e) straight but flexible coil conductors or electrodes along the antenna to serve as EM emitters;
(f) a coil with progressively increasing conductor width or diameter towards or away from the tip of the applicator;
(g) an antenna or electrode with center conductor diameter exposed beyond the outer conductor at the tip region;
(h) an antenna or electrode which has the center conductor exposed beyond the outer conductor and having an increased metal surface area per unit length closer to the tip region to increase the heating toward the tip region;
(i) a coil with different turns ratio per unit length;
(j) diameter variations of the center conductor within the coil length; and
(k) modification of the dielectric material or thickness around the center conductor or coil antenna;
(l) a temperature sensor within the antenna region so as to sense the temperature of the surrounding tissue being heated. While variations f, j, and k are illustrated together in FIG. 4, any of the variations may be used alone or in other combinations to provide desired characteristics of the applicator 14. The various dimensions shown in the figures is greatly exaggerated so as to be visible.

In the exemplary embodiment shown in the figures, a dielectric sheath 70 having a tubular or other suitable configuration may be attached over the antenna 15 so as to avoid direct contact between the antenna and tissue and to create a desired external, electric tissue heating field along the length of the antenna 15. The thickness and configuration of the sheath 70 may be varied as necessary to obtain a desired heating field. While any suitable material may be used, silicone rubber has been found to be acceptable. While direct contact between the metal portions of the applicator 14 and the targeted tissue should normally be avoided, contact may be allowable if sufficient protection is provided to prevent undesirable muscle stimulation, cramping and the like.

Any energy source 54 capable of delivering the energy levels to the antenna 15 through the coaxial cable 56 necessary to heat the targeted tissue to the desired temperature levels may be used. An exemplary power source applicator illustrated in the figures may comprise an oscillator capable of supplying about 70 watts electrical power at a frequency of about 300 to 2450 MHz for microwave-type antennas, or about 100 kHz to 300 MHz for electrode-type or ultrasound-type antennas.

A control and display panel 72 may be used to select and control the treatment time and/or the desired temperature in the targeted tissue. The controller circuit 74 controls the operation of the system 10, including the amount of power supplied by the energy source 54 to the applicator 14 necessary to control and maintain a desired temperature in the targeted tissue being treated. Control signals are sent from the controller circuit 74 to the energy source 54 by control cable 86 so as to maintain the power supplied to the applicators sufficient to generate a tissue temperature between about 41.5 degree Celsius and about 80 degree Celsius. The system controller circuit 74 is connected to the control and display panel 72 for two way communication via cable 150. The control and display panel 72 includes energy on/off switches 78 and 80, a temperature control 82 for selecting the desired operating temperature, and a timer 84 for selecting the treatment time. These control functions can also be provided by other equivalent forms of displays such as switches, buttons, microprocessors, computer terminals and the like.

Figure 5:
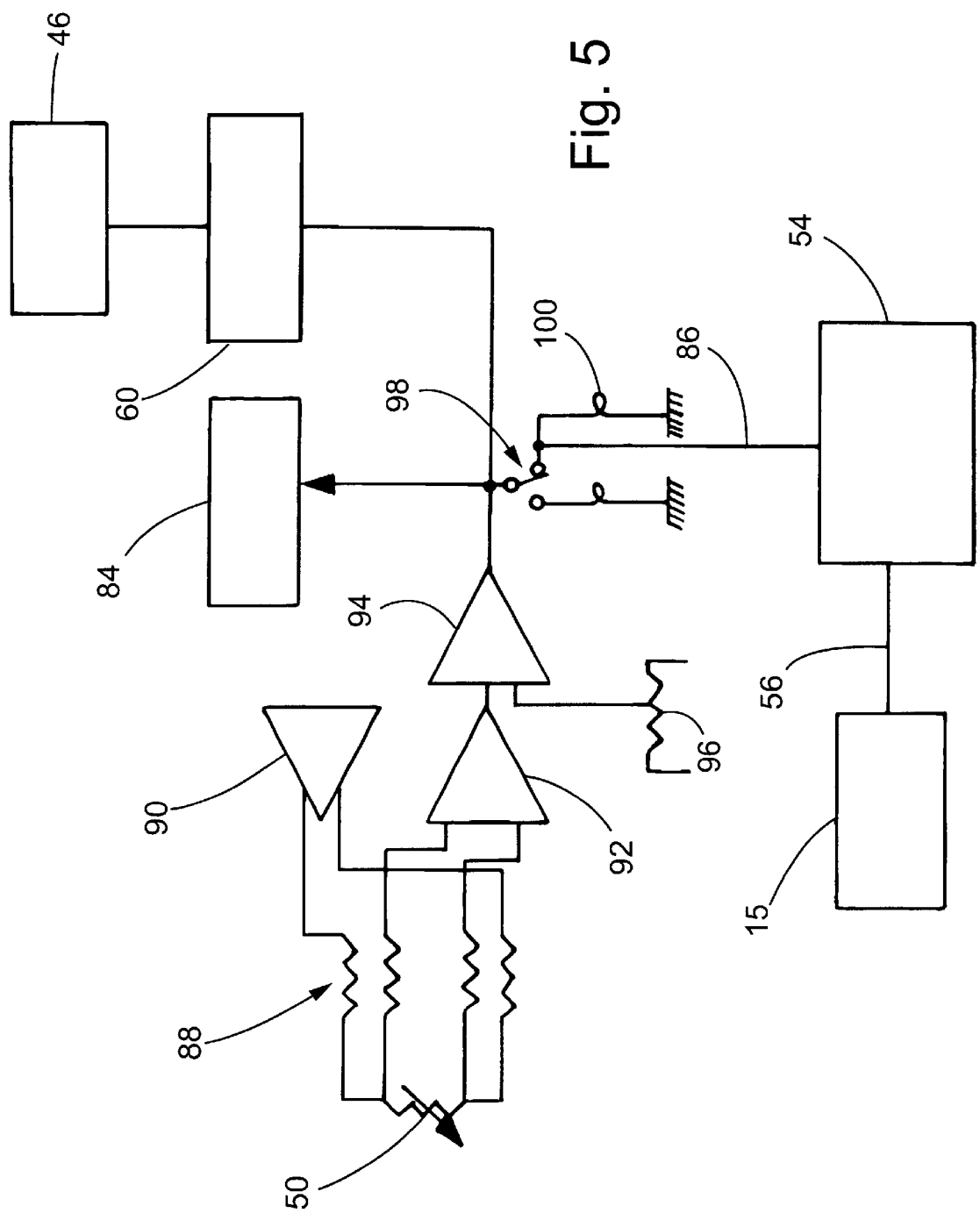
FIG. 5 is a schematic view of an embodiment of a temperature sensor and power source control circuit.

In an exemplary embodiment, a separable insulated temperature sensor 50 measures the temperature of the tissue surrounding the catheter 12, as shown generally in FIG. 1 and by electrical schematic in FIG. 5. The temperature sensor 50 may be placed into the region of the targeted tissue during treatment, preferably by being inserted into a temperature sensor passage 48 of the catheter 12. The passage 48 may be attached to the exterior of the catheter 12, such as by gluing. As with the other passages in the catheter 12, the temperature sensor passage 48 may alternately be a tube embedded in the catheter or may be formed integrally with the catheter. While a single sensor passage 48 and corresponding temperature sensor 50 are illustrated, it will be readily appreciated by those skilled in this art that more than one sensor passage and associated temperature sensor may be utilized if desired.

The exemplary control circuit 74 shown in FIG. 5 may be connected to a temperature sensor 50, by a four lead cable 56. Any suitable temperature sensor may be used but a conventional precalibrated thermistor has been found to be acceptable. The thermistor 50 may be connected to a constant current source 90 and an amplifier 92 for amplifying the thermistor output to a working level. A high gain comparator 94, which has input terminals connected to the amplifier 92 and to a temperature setting potentiometer 96 of the temperature controller 82 (FIG. 1), compares the amplified thermistor output with a desired temperature reference voltage. The high gain comparator 94 has its output connected to the junction of a timer 84 and an electrically controlled pole of a double pole switch 98.

Consequently, when the temperature sensor 50 indicates that the targeted tissue is below the desired temperature, the comparator 94 outputs control signals to activate the switch 98 and, thereby, deliver power to the antenna 15 so as to heat the targeted tissue. When the temperature sensor 50 indicates the targeted tissue is at or above the desired temperature, the comparator 94 outputs control signals to deactivate the switch 98 and, thereby, deactivate the power source 54 so that the antenna 15 does not further heat the targeted tissue.

The timer 84 also controls the switch 98 and the power source 54. Power is transmitted to the antenna 15 when the timer 84 is activated and terminated when the timer 84 is deactivated. In one embodiment, the timer 84 may be activated in response to the initial receipt of power from the comparator 94 for a pre-selected treatment time. At the end of the treatment period, the timer 84 deactivates the switch 98 and, thereby, the power source.

In accordance with certain objects of the invention, the switch 98 may also be controlled by the locator mechanism 60 which deactivates the switch (or provides other appropriate signals to the operator) in response to conditions, such as deflation of the balloon, which indicate the possibility of movement of the applicator 14. In one exemplary embodiment, the locator mechanism monitors the back pressure of the balloon 31 and/or pressurized fluid passage 38. While the back pressure remains within a predetermined range, the switch remains activated and power is supplied to the applicator 14. However, the locator mechanism deactivates the switch 98 in response to pressure decreases in the balloon 31 or fluid passage which may indicate movement of the applicator 14.

The switch 98, of course, may also be manually controlled by the control switches 78 and 80. When the switch 98 is activated as shown in FIG. 5, a control signal is output on lead 100 to activate the power source 54. Conversely, when the switch 80 is deactivated, the power source 54 is deactivated.

While an exemplary embodiment of the microwave control circuit 74, the control and display panel 72, and the temperature sensor circuit 88 has been illustrated and described herein, it will be readily apparent to those skilled in this art that a variety of modifications could be made to this overall control system if desired. For example, the timer 84, comparator 94, temperature setting potentiometer 96, control switch 98, or other portions of the control circuit can be microprocessor controlled or otherwise automated if desired. It will be appreciated that additional temperature sensors inserted through corresponding tube, leads and control circuits (not shown) may be added as additional temperature monitors.

In use, the catheter 12 is inserted through the patient's urethral passage, the prostate P, and into the bladder B, as schematically shown in FIG. 6. It is thus important that the catheter 12 be flexible enough to be easily inserted through the urethral passage. When the distal end 13 of the catheter 12 is in the bladder, pressurized fluid is introduced through valve 46 and opening 44 into passage 38 to inflate balloon 31 within the bladder. With the balloon 31 inflated in the bladder B, the catheter 12 is pulled slightly outwardly so that the balloon 31 seats in the neck N of the bladder B. This positively locates and positions the catheter 12, as well as the antenna 15, with respect to the bladder and prostate immediately adjacent to the bladder as shown in FIG. 6. In this position of the catheter 12 and the antenna 15 remains constant with respect to the bladder and prostate regardless of any variation in length of the urethral passage during treatment. While catheter 12 is positioned in the bladder B, drainage passage 34 permits urine drainage tube from the bladder, out the drainage opening 42 to a liquid waste receptacle (not shown).

In the exemplary embodiment, the applicator 14 creates an external, electromagnetic heating field which extends for a desired length along the antenna 15 to create a heating portion of the applicator 14. In some embodiments, this heating field may be approximately uniform along the length of the antenna 15.

In operation, with the apparatus properly positioned as described above, the timer 84 and the temperature control 82 are selected as desired, and the generator 54 is activated by switch 98. The applicator 14 radiates heat into the targeted tissue of the prostate gland extending along the antenna 15 of the applicator 14 until the desired temperature is reached and/or the treatment time expires. When the desired tissue temperature is reached, the comparator 94 outputs control signals to the power source 54 to control the power output to the applicator 14 to maintain the temperature substantially constant for the selected treatment time period. At the end of the treatment time, the power source 54 is automatically turned off by timer 84. However, the power 54 can be turned off at any time using the "off" switch 80. As described above, the applicator 14 deactivates the power source or sends another appropriate signal to the operator should conditions exist that permit movement of the antenna 15 from the desired location.

Thus, it will be seen that a novel and improved energy radiation device for medical hyperthermic treatments has been provided which attains the aforementioned objects. Various additional modifications of the embodiments specifically illustrated and described herein will be apparent to those skilled in the art, particularly in light of the teachings of this invention. The invention should not be construed as limited to the specific form shown and described, but instead is set forth in the following claims.

What is claimed is:

1. An energy radiation applicator apparatus for hyperthermic treatment of targeted tissue in a patient, comprising:
   a catheter for insertion into the patient;
   an antenna operatively carried by the catheter and an energy source sufficient for elevating the temperature of targeted tissue in proximity to the antenna to a preselected temperature and for maintaining the preselected temperature during treatment;
   a positioning mechanism operatively attached to the catheter, separate from the antenna, for positioning the antenna in desired proximity to the targeted tissue to be treated;
   a temperature sensor operatively attached to the catheter and in operative association with the antenna for measuring the temperature of the targeted tissue; and
   a locator for determining whether the antenna remains at the desired position, wherein the locator measures the relative movement between the catheter and the patient to determine whether the antenna has moved from the desired position, and wherein the locator is operatively attached to the energy source for deactivating the energy source when the antenna moves from the desired position.

2. An energy radiation applicator apparatus according to claim 1 wherein the locator monitors the condition of the positioning mechanism and is operatively attached to the energy source so as to deactivate the energy source when the condition of the positioning mechanism permits movement of the antenna from the desired position.

3. An energy radiation applicator apparatus according to claim 1 wherein the locator monitors the condition of the positioning mechanism and is operatively attached to a signal device and the signal device generates a signal when the condition of the positioning mechanism permits movement of the antenna from the desired position.

4. An energy radiation applicator apparatus according to claim 1 wherein the locator measures the relative movement between the catheter and the patient to determine whether the antenna has moved from the desired position, and wherein the locator is operatively attached to a signal device which generates a signal when the antenna moves from the desired position.

5. An energy radiation applicator apparatus comprising:
   a catheter;
   an antenna operatively carried by the catheter and an energy source sufficient for elevating the temperature of targeted tissue in proximity to the antenna to a preselected temperature and for maintaining the preselected temperature during treatment;
   a positioning mechanism operatively attached to the catheter, for positioning the antenna at a desired position in proximity to the targeted tissue to be treated;
   a temperature sensor operatively attached to the catheter and in operative association with the antenna for measuring the temperature of the targeted tissue; and
   a locator for determining whether the antenna remains at the desired position, wherein the positioning mechanism comprises an inflatable balloon operatively attached to the catheter so at least a portion of the balloon may extend into the patient's bladder, and the catheter comprises a passage communicating with the balloon and a source of pressurized fluid so the balloon can be inflated and position the catheter when the antenna is at the desired position, and wherein the locator measures relative movement between the catheter and the patient to determine whether the antenna has moved from the desired position.

6. An energy radiation applicator apparatus comprising:
   a catheter;
   an antenna operatively carried by the catheter and an energy source sufficient for elevating the temperature of targeted tissue in proximity to the antenna to a preselected temperature and for maintaining the preselected temperature during treatment;
   a positioning mechanism operatively attached to envelop a portion of the catheter separate from the antenna, for positioning the antenna at a desired position in proximity to the targeted tissue to be treated, wherein the positioning mechanism comprises an inflatable balloon operatively attached to the catheter so at least a portion of the balloon may extend into a patient's bladder, and the catheter comprises a passage communicating with the balloon and a source of pressurized fluid so the balloon can be inflated and position the catheter when the antenna is at the desired position;
   a temperature sensor operatively attached to the catheter and in operative association with the antenna for measuring the temperature of the targeted tissue; and
   a locator for determining whether the antenna remains at the desired position, wherein the locator comprises a pressure monitor operatively attached to the balloon for measuring the pressure in the balloon, and wherein the locator measures relative movement between the catheter and the patient to determine whether the antenna has moved from the desired position.

7. An energy radiation applicator apparatus comprising:
   a catheter;
   an antenna operatively carried by the catheter and an energy source sufficient for elevating the temperature of targeted tissue in proximity to the applicator to a preselected temperature and for maintaining the preselected temperature during treatment;
   a positioning mechanism operatively attached to the catheter, for positioning the antenna at a desired position in proximity to the targeted tissue to be treated, wherein the positioning mechanism comprises an inflatable balloon operatively attached to the catheter so at least a portion of the balloon may extend into a patient's bladder, and the catheter comprises a passage communicating with the balloon and a source of pressurized fluid so the balloon can be inflated and position the catheter when the antenna is at the desired position;
   a temperature sensor operatively attached to the catheter and in operative association with the antenna for measuring the temperature of the targeted tissue; and
   a locator for determining whether the antenna remains at the desired position, wherein the locator comprises a pressure monitor operatively attached to the balloon for measuring the pressure in the balloon, wherein the pressure monitor is operatively attached to the energy source and deactivates the energy source when the balloon pressures decreases below a predetermined pressure that permits movement of the antenna from the desired position relative to the targeted tissue, and wherein the locator measures relative movement between the catheter and the patient to determine whether the antenna has moved from the desired position.

8. An energy radiation applicator apparatus comprising:
a catheter;
an antenna operatively carried by the catheter and an energy source sufficient for elevating the temperature of targeted tissue in proximity to the antenna to a preselected temperature and for maintaining the preselected temperature during treatment;
a positioning mechanism operatively attached to the catheter for positioning the antenna at a desired position in proximity to the targeted tissue to be treated, wherein the positioning mechanism comprises an inflatable balloon operatively attached to the catheter so at least a portion of the balloon may extend into a patient's bladder, and the catheter comprises a passage communicating with the balloon and a source of pressurized fluid so the balloon can be inflated and position the catheter when the antenna is at the desired position;
a temperature sensor operatively attached to the catheter and in operative association with the antenna for measuring the temperature of the targeted tissue; and
a locator for determining whether the antenna remains at the desired position comprising a pressure monitor operatively attached to the balloon for measuring the pressure in the balloon, wherein the pressure monitor is operatively attached to a signal device, and the signal device generates a signal when the balloon pressures decreases below a predetermined pressure that permits movement of the antenna from the desired position relative to the targeted tissue, and wherein the locator measures relative movement between the catheter and the patient to determine whether the antenna has moved from the desired position.

9. An energy radiation applicator apparatus comprising:
a catheter;
an antenna operatively carried by the catheter and an energy source sufficient for elevating the temperature of targeted tissue in proximity to the antenna to a preselected temperature and for maintaining the preselected temperature during treatment;
a positioning mechanism operatively attached to the catheter, for positioning the antenna at a desired position in proximity to the targeted tissue to be treated, wherein the positioning mechanism comprises a balloon including a material located substantially inside the balloon during proper operation of the apparatus;
a temperature sensor operatively attached to the catheter and in operative association with the antenna for measuring the temperature of the targeted tissue; and
a locator for determining whether the antenna remains at the desired position, wherein the locator is operatively attached to the energy source and optically measures the presence of the material outside the balloon indicating that the balloon has at least partially deflated permitting movement of the catheter, and wherein the locator deactivates the energy source when the locator measures the presence of the material outside the balloon.

10. An energy radiation applicator apparatus comprising:
a catheter;
an antenna operatively carried by the catheter and an energy source sufficient for elevating the temperature of targeted tissue in proximity to the antenna to a preselected temperature and for maintaining the preselected temperature during treatment;
a positioning mechanism operatively attached to the catheter, for positioning the antenna at a desired position in proximity to the targeted tissue to be treated, wherein the positioning mechanism comprises a balloon including a material located substantially inside the balloon during proper operation of the apparatus;
a temperature sensor operatively attached to the catheter and in operative association with the antenna for measuring the temperature of the targeted tissue; and
a locator for determining whether the antenna remains at the desired position, wherein the locator is operatively attached to a signal device and optically measures the presence of the material outside the balloon indicating that the balloon has at least partially deflated permitting movement of the catheter, the locator activates the signal device when the locator measures the presence of the material outside the balloon.

11. A method for hyperthermic treatment of target tissue in a patient's body comprising:
operatively associating an antenna with a catheter and with an energy source sufficient to elevate the temperature of the targeted tissue to a preselected temperature and for maintaining the preselected temperature during treatment;
inserting the catheter into the patient's body so the antenna carried by the catheter is at a desired position in proximity to the targeted tissue to be treated;
positioning the antenna at the desired position by disposing a positioning mechanism in a location separate from the targeted tissue;
determining whether the antenna remains in the desired position by measuring relative movement between the catheter and the patient; and
indicating when the antenna may move from the desired position.

12. A method according to claim 11 comprising indicating when the antenna may move from the desired position by deactivating the energy source.

13. A method according to claim 12 comprising indicating when the antenna may move from the desired position by deactivating the energy source when the relative movement exceeds a predetermined amount.

14. A method according to claim 12 comprising indicating when the antenna may move from the desired position by generating a signal when the relative movement exceeds a predetermined amount.

15. A method for hyperthermic treatment of target tissue in a patient's body comprising:
operatively associating an antenna with a catheter and with an energy source sufficient to elevate the temperature of the targeted tissue to a preselected temperature and for maintaining the preselected temperature during treatment;
inserting the catheter into the patient's body so the antenna carried by the catheter is at a desired-position in proximity to the targeted tissue to be treated;
inserting an inflatable balloon operatively attached to the catheter for positioning and maintaining the antenna in the desired position into the patient's urethra so at least a portion of the balloon may extend into the patient's bladder;
positioning the antenna at the desired position;
positioning the catheter when the antenna is at the desired position by inflating the balloon through a pressurized fluid passage communicating with the balloon and a source of pressurized fluid;
determining whether the antenna remains in the desired position by measuring relative movement between the catheter and the patient; and indicating when the antenna may move from the desired position.

16. A method for hyperthermic treatment of target tissue in a patient's body comprising:

operatively associating an antenna with a catheter and with an energy source sufficient to elevate the temperature of the targeted tissue to a preselected temperature and for maintaining the preselected temperature during treatment;

inserting the catheter into the patient's body so the antenna carried by the catheter is at a desired position in proximity to the targeted tissue to be treated;

inserting an inflatable balloon operatively attached to the catheter for positioning and maintaining the antenna in the desired position into the patient's urethra so at least a portion of the balloon may extend into the patient's bladder;

positioning the antenna at the desired position;

positioning the catheter when the antenna is at the desired position by inflating the balloon through a pressurized fluid passage communicating with the balloon and a source of pressurized fluid; and determining whether the antenna remains at the desired position by measuring relative movement between the catheter and the patient;

indicating when the antenna may move from the desired position.

17. A method for hyperthermic treatment of target tissue in a patient's body comprising:

operatively associating an antenna with a catheter and with an energy source sufficient to elevate the temperature of the targeted tissue to a preselected temperature and for maintaining the preselected temperature during treatment;

inserting the catheter into the patient's body so the antenna carried by the catheter is at a desired position in proximity to the targeted tissue to be treated;

inserting an inflatable balloon operatively attached to the catheter for positioning and maintaining the antenna in the desired position into the patient's urethra so at least a portion of the balloon may extend into the patient's bladder;

positioning the antenna at the desired position;

positioning the catheter when the antenna is at the desired position by inflating the balloon through a pressurized fluid passage communicating with the balloon and a source of pressurized fluid; and determining whether the antenna remains at the desired position by measuring relative movement between the catheter and the patient;

indicating when the antenna may move from the desired position by deactivating the energy source when the balloon pressures decreases below a predetermined pressure that permits the antenna to move from the desired position relative to the targeted tissue.

18. A method for hyperthermic treatment of target tissue in a patient's body comprising:

operatively associating an antenna with a catheter and with an energy source sufficient to elevate the temperature of the targeted tissue to a preselected temperature and for maintaining the preselected temperature during treatment;

inserting the catheter into the patient's body so the antenna carried by the catheter is at a desired position in proximity to the targeted tissue to be treated;

inserting an inflatable balloon operatively attached to the catheter for positioning and maintaining the antenna in the desired position into the patient's urethra so at least a portion of the balloon may extend into the patient's bladder;

positioning the antenna at the desired position;

positioning the catheter when the antenna is at the desired position by inflating the balloon through a pressurized fluid passage communicating with the balloon and a source of pressurized fluid; and determining whether the antenna remains at the desired position by measuring relative movement between the catheter and the patient;

indicating when the antenna may move from the desired position by generating a signal when the balloon pressures decreases below a predetermined pressure that permits the antenna to move from the desired position relative to the targeted tissue.

19. A method for hyperthermic treatment of target tissue in a patient's body comprising:

operatively associating an antenna with a catheter and with an energy source sufficient to elevate the temperature of the targeted tissue to a preselected temperature and for maintaining the preselected temperature during treatment;

inserting the catheter into the patient's body so the antenna carried by the catheter is at a desired position in proximity to the targeted tissue to be treated;

inserting an inflatable balloon operatively attached to the catheter for positioning and maintaining the antenna in the desired position into the patient's urethra so at least a portion of the balloon may extend into the patient's bladder;

positioning the antenna at the desired position;

positioning the catheter when the antenna is at the desired position by inflating the balloon through a pressurized fluid passage communicating with the balloon and a source of pressurized fluid;

determining whether the antenna remains in the desired position by placing a material substantially inside the balloon and optically sensing the presence of a material outside the balloon indicating that the balloon has at least partially deflated so as to permit movement of the applicator; and indicating when the antenna may move from the desired position.

20. A method for hyperthermic treatment of target tissue in a patient's body comprising:

operatively associating an antenna with a catheter and with an energy source sufficient to elevate the temperature of the targeted tissue to a preselected temperature and for maintaining the preselected temperature during treatment;

inserting the catheter into the patient's body so the antenna carried by the catheter is at a desired position in proximity to the targeted tissue to be treated;

inserting an inflatable balloon operatively attached to the catheter for positioning and maintaining the antenna in the desired position into the patient's urethra so at least a portion of the balloon may extend into the patient's bladder;

positioning the antenna at the desired position;

positioning the catheter when the antenna is at the desired position by inflating the balloon through a pressurized fluid passage communicating with the balloon and a source of pressurized fluid;

determining whether the antenna remains in the desired position by placing a material substantially inside the balloon and optically sensing the presence of a material outside the balloon indicating that the balloon has at least partially deflated so as to permit movement of the applicator; and indicating when the antenna may move from the desired position by deactivating the power source when the material escapes from the balloon.

21. A method for hyperthermic treatment of target tissue in a patient's body comprising:

operatively associating an antenna with a catheter and with an energy source sufficient to elevate the temperature of the targeted tissue to a preselected temperature and for maintaining the preselected temperature during treatment;

inserting the catheter into the patient's body so the antenna carried by the catheter is at a desired position in proximity to the targeted tissue to be treated;

inserting an inflatable balloon operatively attached to the catheter for positioning and maintaining the antenna in the desired position into the patient's urethra so at least a portion of the balloon may extend into the patient's bladder;

positioning the antenna at the desired position;

positioning the catheter when the antenna is at the desired position by inflating the balloon through a pressurized fluid passage communicating with the balloon and a source of pressurized fluid;

determining whether the antenna remains in the desired position by placing a material substantially inside the balloon and optically sensing the presence of a material outside the balloon indicating that the balloon has at least partially deflated so as to permit movement of the applicator; and indicating when the antenna may move from the desired position by generating a signal when the material escapes from the balloon.

22. An energy radiation applicator apparatus for hyperthermic treatment of targeted tissue in a patient, comprising:

a catheter for insertion into the patient;

an antenna operatively carried by the catheter and an energy source sufficient for elevating the temperature of targeted tissue in proximity to the antenna to a preselected temperature and for maintaining the preselected temperature during treatment;

a positioning mechanism operatively attached to the catheter for positioning the antenna in desired proximity to the targeted tissue to be treated; and a locator for measuring relative movement between the catheter and the patient to determine whether the antenna has moved from the desired position.

23. The energy radiation applicator apparatus of claim 22 wherein the locator is operatively attached to the energy source for deactivating the energy source when the relative movement exceeds a predetermined amount.

24. The energy radiation applicator apparatus of claim 22 comprising:

a temperature operatively attached to the catheter and in operative association with the antenna for measuring the temperature of the targeted tissue.

25. The energy radiation applicator apparatus of claim 22 wherein the positioning mechanism is separate from the antenna.

26. A method for hyperthermic treatment of target tissue in a patient's body comprising:

operatively associating an antenna with a catheter and with an energy source sufficient to elevate the temperature of the targeted tissue to a preselected temperature and for maintaining the preselected temperature during treatment;

inserting the catheter into the patient's body so the antenna carried by the catheter is at a desired position in proximity to the targeted tissue to be treated; and determining whether the antenna remains in the desired position during treatment by measuring relative movement between the catheter and the patient.

27. The method of claim 26 comprising:

positioning the antenna at the desired position by disposing a positioning mechanism in a location separate from the target tissue.

28. The method of claim 26 comprising:

indicating the antenna may have moved from the desire position when the relative movement exceeds a predetermined amount.

29. The method of claim 26 comprising:

deactivating the energy source when the relative movement exceeds a predetermined amount.

30. A method for hyperthermic treatment of prostrate tissue in a patient's body comprising:

operatively associating an antenna with a catheter and with an energy source sufficient to elevate the temperature of the prostrate tissue to a preselected temperature and for maintaining the preselected temperature during treatment;

operatively associating a balloon near a distal end of the catheter;

inserting the catheter into the patient's urethral passage until the distal end of the catheter is in the patient's bladder;

inflating the balloon within the bladder so that the balloon seats on a neck of the bladder, the action of the balloon inflating against the neck causing the catheter to be pulled slightly outwardly to positively locate the antenna in a desired position with respect to the prostrate tissue during treatment determining whether the antenna remains in the desired position during treatment by measuring relative movement between the catheter and the patient.

31. The method of claim 20 comprising:

deactivating the energy source when the relative movement exceeds a predetermined amount.

* * * * *

UNITED STATES PATENT AND TRADEMARK OFFICE
CERTIFICATE OF CORRECTION

PATENT NO. : 6,640,138 B1  
DATED : October 28, 2003  
INVENTOR(S) : Theron N. Schaefermeyer It is certified that error appears in the above-identified patent and that said Letters Patent is hereby corrected as shown below:

Column 16,
Line 56, after "claim", please delete "20" insert -- 30 --.

Signed and Sealed this

Fourth Day of May, 2004

JON W. DUDAS
*Acting Director of the United States Patent and Trademark Office*